US011541018B2

(12) United States Patent
Lee et al.

(10) Patent No.: US 11,541,018 B2
(45) Date of Patent: Jan. 3, 2023

(54) ADHESIVE MATRIX WITH HYDROPHILIC AND HYDROPHOBIC DOMAINS AND A THERAPEUTIC AGENT

(71) Applicant: Corium, LLC, Boston, MA (US)

(72) Inventors: Eun Soo Lee, Redwood City, CA (US); Amit K. Jain, Milpitas, CA (US); Parminder Singh, Union City, CA (US)

(73) Assignee: Corium, LLC, Boston, MA (US)

( * ) Notice: Subject to any disclaimer, the term of this patent is extended or adjusted under 35 U.S.C. 154(b) by 0 days.

(21) Appl. No.: 16/312,252

(22) PCT Filed: Jun. 23, 2017

(86) PCT No.: PCT/US2017/038934
§ 371 (c)(1),
(2) Date: Dec. 20, 2018

(87) PCT Pub. No.: WO2017/223402
PCT Pub. Date: Dec. 28, 2017

(65) Prior Publication Data
US 2019/0231709 A1 Aug. 1, 2019

Related U.S. Application Data

(60) Provisional application No. 62/353,891, filed on Jun. 23, 2016.

(51) Int. Cl.
| | | |
|---|---|---|
| *A61K 9/50* | (2006.01) | |
| *A61K 35/742* | (2015.01) | |
| *C12N 1/20* | (2006.01) | |
| *C08G 77/12* | (2006.01) | |
| *C08G 77/20* | (2006.01) | |
| *C08G 77/08* | (2006.01) | |
| *A61K 9/70* | (2006.01) | |
| *A61K 31/167* | (2006.01) | |
| *A61K 31/216* | (2006.01) | |
| *A61K 31/445* | (2006.01) | |
| *A61K 31/4045* | (2006.01) | |
| *A61K 47/32* | (2006.01) | |

(52) U.S. Cl.
CPC .......... *A61K 9/7061* (2013.01); *A61K 9/7053* (2013.01); *A61K 31/167* (2013.01); *A61K 31/216* (2013.01); *A61K 31/4045* (2013.01); *A61K 31/445* (2013.01); *A61K 47/32* (2013.01)

(58) Field of Classification Search
CPC ............... A61K 31/167; A61K 31/216; A61K 31/4045; A61K 31/445; A61K 47/32; A61K 9/7053; A61K 9/7061
See application file for complete search history.

(56) References Cited

U.S. PATENT DOCUMENTS

| | | |
|---|---|---|
| 3,391,142 A | 7/1968 | Mills et al. |
| 3,546,141 A | 12/1970 | Washburn et al. |
| 3,549,016 A | 12/1970 | Rigopulos |
| 4,122,193 A | 10/1978 | Scherm et al. |
| 4,273,774 A | 6/1981 | Scherm |
| 4,752,478 A | 6/1988 | Bondi et al. |
| 4,781,924 A | 11/1988 | Lee et al. |
| 4,837,027 A | 6/1989 | Lee et al. |
| 4,849,224 A | 7/1989 | Chang et al. |
| 4,880,633 A | 11/1989 | Loper et al. |
| 4,886,812 A | 12/1989 | Griss et al. |
| 4,895,841 A | 1/1990 | Sugimoto et al. |
| 5,026,556 A | 6/1991 | Drust et al. |
| 5,061,703 A | 10/1991 | Bormann et al. |
| 5,123,900 A | 6/1992 | Wick |
| 5,132,115 A | 7/1992 | Wolter et al. |
| 5,202,128 A | 4/1993 | Morelia et al. |
| 5,252,588 A | 10/1993 | Azuma et al. |
| 5,296,512 A | 3/1994 | Beier et al. |
| 5,362,497 A | 11/1994 | Yamada et al. |
| 5,424,077 A | 6/1995 | Lajoie |
| 5,614,560 A | 3/1997 | Lipton |
| 5,635,203 A | 6/1997 | Gale et al. |
| 5,662,925 A | 9/1997 | Ebert et al. |
| 5,730,900 A | 3/1998 | Higo et al. |
| 5,730,999 A | 3/1998 | Lehmann et al. |
| 5,843,468 A | 12/1998 | Burkoth et al. |

(Continued)

FOREIGN PATENT DOCUMENTS

| | | |
|---|---|---|
| CA | 2332012 A1 | 11/1999 |
| CN | 1174031 A | 2/1998 |

(Continued)

OTHER PUBLICATIONS

US 9,095,635 B2, 08/2015, Willmann et al. (withdrawn)
Aida et al., "Adhesive patch useful in pharmaceuticals, for delivering drugs, provides single surface of support with adhesive layer, where adhesive layer contains drug in solution stae and crystalline state", Database WPI, AN 2008-F37689 (2013).
Ashall, "Tobacco Facts #4: Smokers are freebasing nicotine!—The Great Tobacco Plague", Dr Frank Ashails Blog, Retreived from the Internet: https://biochemdr1.wordpress.com/2013/11/30/tobacco-fact-4-somkers-are-freebasing-nicotine/, 7 pages (Nov. 30, 2013).
Brantseva et al., "Rheological and adhesive properties of PIB-based pressure-sensitive adhesives with montmorillonite-type nanofillers", European Polymer Journal, vol. 76, pp. 228-244 (2016).

(Continued)

*Primary Examiner* — Anna R Falkowitz
(74) *Attorney, Agent, or Firm* — McDermott Will & Emery LLP; Judy M. Mohr; Brennen P. Baylor

(57) ABSTRACT

An adhesive matrix and adhesive formulation are described. The adhesive matrix is comprised of a hydrophilic domain and a hydrophobic domain, and a therapeutically active agent contained in the matrix in a supersaturated, stable, condition. The hydrophilic domain and the hydrophobic domain are co-soluble in a solvent system, to provide a homogeneous blend in which the active agent is solubilized. The proportion of the hydrophilic domain and hydrophobic domain is selected to optimize, or maximize, solubility of active agent in the matrix.

7 Claims, No Drawings

(56) References Cited

U.S. PATENT DOCUMENTS

| | | |
|---|---|---|
| 5,866,585 A | 2/1999 | Fogel |
| 5,958,919 A | 9/1999 | Olney et al. |
| 6,004,578 A | 12/1999 | Lee et al. |
| 6,255,348 B1 | 7/2001 | Elstner |
| 6,383,471 B1 | 5/2002 | Chen et al. |
| 6,512,010 B1 | 1/2003 | Gale et al. |
| 6,521,639 B1 | 2/2003 | Murahashi et al. |
| 6,746,689 B2 | 6/2004 | Fischer et al. |
| 6,923,988 B2 | 8/2005 | Patel et al. |
| 6,929,801 B2 | 8/2005 | Klose et al. |
| 7,097,853 B1 | 8/2006 | Garbe et al. |
| 7,176,185 B2 | 2/2007 | Hilfinger et al. |
| 7,250,394 B2 | 7/2007 | Nedergaard |
| 7,320,802 B2 | 1/2008 | Ryde et al. |
| 7,335,379 B2 | 2/2008 | Carrara et al. |
| 7,462,743 B2 | 12/2008 | Merli et al. |
| 7,670,838 B2 | 3/2010 | Deisseroth et al. |
| 7,682,628 B2 | 3/2010 | Singh |
| 7,744,918 B2 | 6/2010 | Yamaguchi et al. |
| 7,858,114 B2 | 12/2010 | Ito |
| 7,888,422 B2 | 2/2011 | Jackson et al. |
| 8,058,291 B2 | 11/2011 | Went et al. |
| 8,168,209 B2 | 5/2012 | Went et al. |
| 8,246,978 B2 | 8/2012 | Kydonieus et al. |
| 8,252,321 B2 | 8/2012 | Dipierro et al. |
| 8,283,379 B2 | 10/2012 | Went et al. |
| 8,362,085 B2 | 1/2013 | Went et al. |
| 8,512,742 B2 | 8/2013 | Amano et al. |
| 8,614,274 B2 | 12/2013 | Jackson et al. |
| 8,673,338 B2 | 3/2014 | Bleier |
| 8,784,879 B2 | 7/2014 | Singh et al. |
| 8,815,281 B2 | 8/2014 | Kanios et al. |
| 8,840,922 B2 | 9/2014 | Kawakami et al. |
| 8,840,935 B2 | 9/2014 | Haber et al. |
| 8,874,879 B2 | 10/2014 | Ge et al. |
| 9,012,511 B2 | 4/2015 | Neville et al. |
| 9,248,104 B2 | 2/2016 | Valia et al. |
| 9,622,986 B2 | 4/2017 | Im et al. |
| 9,993,466 B2 | 6/2018 | Lee et al. |
| 10,016,372 B2 | 7/2018 | Singh et al. |
| 10,300,025 B2 | 5/2019 | Lee et al. |
| 10,307,379 B2 | 6/2019 | Lee et al. |
| 11,103,463 B2 | 8/2021 | Lee et al. |
| 2001/0031787 A1 | 10/2001 | Hsu et al. |
| 2002/0192243 A1 | 12/2002 | Hsu et al. |
| 2003/0170308 A1 | 9/2003 | Cleary et al. |
| 2004/0018241 A1 | 1/2004 | Houze et al. |
| 2004/0022835 A1 | 2/2004 | Pai et al. |
| 2004/0033254 A1 | 2/2004 | Song et al. |
| 2004/0087658 A1 | 5/2004 | Moebius |
| 2004/0180080 A1 | 9/2004 | Furusawa et al. |
| 2005/0113458 A1 | 5/2005 | Gupta et al. |
| 2006/0035888 A1 | 2/2006 | Jonas et al. |
| 2006/0188558 A1 | 8/2006 | Jackson et al. |
| 2006/0205822 A1 | 9/2006 | Jonas et al. |
| 2007/0184097 A1 | 8/2007 | Kurita et al. |
| 2008/0004329 A1 | 1/2008 | Jamieson et al. |
| 2008/0038328 A1 | 2/2008 | Higo et al. |
| 2008/0107719 A1 | 5/2008 | Likitlersuang et al. |
| 2008/0131490 A1 | 6/2008 | Hanatani et al. |
| 2008/0131491 A1 | 6/2008 | Hanatani et al. |
| 2008/0138388 A1 | 6/2008 | Aida et al. |
| 2009/0062754 A1 | 3/2009 | Tang |
| 2009/0081259 A1 | 3/2009 | Jonas et al. |
| 2009/0124659 A1 | 5/2009 | Moebius |
| 2009/0156639 A1 | 6/2009 | Trippodi-Murphy et al. |
| 2009/0175929 A1 | 7/2009 | Terahara et al. |
| 2009/0291127 A1 | 11/2009 | Wen et al. |
| 2010/0121290 A1 | 5/2010 | Rasmussen et al. |
| 2010/0178037 A1 | 7/2010 | Chen et al. |
| 2010/0227852 A1 | 9/2010 | Moebius |
| 2010/0291186 A1 | 11/2010 | Singh et al. |
| 2011/0056863 A1 | 3/2011 | Sekiya et al. |
| 2011/0059141 A1 | 3/2011 | Ito |
| 2011/0059169 A1 | 3/2011 | Went et al. |
| 2011/0066120 A1 | 3/2011 | Lee |
| 2011/0111013 A1 | 5/2011 | Salman et al. |
| 2011/0244023 A1 | 10/2011 | Cottrell et al. |
| 2011/0313372 A1 | 12/2011 | Eifler et al. |
| 2012/0121729 A1 | 5/2012 | Paterson et al. |
| 2012/0245537 A1 | 9/2012 | Horstmann et al. |
| 2012/0321690 A1 | 12/2012 | Toshimitsu et al. |
| 2012/0323190 A1 | 12/2012 | Ito |
| 2013/0053358 A1 | 2/2013 | Aida et al. |
| 2013/0064868 A1 | 3/2013 | Okazaki et al. |
| 2013/0211353 A1 | 8/2013 | Toshimitsu et al. |
| 2013/0331803 A1 | 12/2013 | Fleschhut et al. |
| 2014/0052081 A1 | 2/2014 | Yang et al. |
| 2014/0114049 A1 | 4/2014 | Jiao et al. |
| 2014/0148456 A1* | 5/2014 | Likitlersuang ....... A61K 31/498 514/236.2 |
| 2014/0256690 A1 | 9/2014 | Arkady et al. |
| 2014/0276479 A1 | 9/2014 | Nguyen et al. |
| 2014/0322284 A1 | 10/2014 | Singh et al. |
| 2014/0370076 A1 | 12/2014 | Choi et al. |
| 2015/0098980 A1 | 4/2015 | Pongpeerapat et al. |
| 2016/0051486 A1 | 2/2016 | Choi et al. |
| 2016/0256552 A1 | 9/2016 | Yamasaki |
| 2017/0202830 A1 | 7/2017 | Stinchcomb et al. |
| 2017/0360908 A1 | 12/2017 | Shishido et al. |
| 2018/0028461 A1 | 2/2018 | Singh et al. |
| 2018/0028462 A1 | 2/2018 | Lee et al. |
| 2018/0028463 A1 | 2/2018 | Lee et al. |
| 2018/0028466 A1 | 2/2018 | Lee et al. |
| 2018/0028467 A1 | 2/2018 | Singh et al. |
| 2018/0028512 A1 | 2/2018 | Lee et al. |
| 2018/0028663 A1 | 2/2018 | Lee et al. |
| 2018/0185298 A1 | 7/2018 | Jain et al. |
| 2018/0235901 A1 | 8/2018 | Lee et al. |
| 2019/0029971 A1 | 1/2019 | Lee et al. |
| 2019/0247320 A1 | 8/2019 | Lee et al. |

FOREIGN PATENT DOCUMENTS

| | | |
|---|---|---|
| CN | 1895242 B | 1/2007 |
| CN | 102048678 A | 5/2011 |
| CN | 105693556 A | 6/2016 |
| EP | 0296560 A2 | 12/1988 |
| EP | 0377518 A2 | 7/1990 |
| EP | 0481443 A1 | 10/1991 |
| EP | 0540623 B1 | 9/1994 |
| EP | 1423100 A1 | 6/2004 |
| EP | 1682109 B1 | 10/2008 |
| EP | 2016941 A1 | 1/2009 |
| EP | 2090310 A1 | 8/2009 |
| EP | 2098233 A1 | 9/2009 |
| EP | 2098235 A1 | 9/2009 |
| EP | 2260839 A2 | 12/2010 |
| EP | 2514415 A1 | 10/2012 |
| EP | 2638906 A1 | 9/2013 |
| EP | 2818161 A1 | 12/2014 |
| IE | 61005 B1 | 9/1994 |
| JP | H06-199659 A | 7/1994 |
| JP | 2009-013171 A | 1/2009 |
| JP | 2009-203213 A | 9/2009 |
| JP | 2013-075856 A | 4/2013 |
| JP | 2015-151370 A | 8/2015 |
| KR | 2009-0101667 A | 9/2009 |
| WO | WO 1995/018603 A1 | 7/1995 |
| WO | WO 1996/019205 A1 | 6/1996 |
| WO | WO 1996/040087 A2 | 12/1996 |
| WO | WO 2003/020248 A1 | 3/2003 |
| WO | WO 2003/055471 A1 | 7/2003 |
| WO | WO 2005/079779 A1 | 9/2005 |
| WO | WO 2006/091442 A2 | 8/2006 |
| WO | WO 2007/129427 A1 | 11/2007 |
| WO | WO 2007/132476 A2 | 11/2007 |
| WO | WO 2008/021113 A2 | 2/2008 |
| WO | WO 2009/032184 A1 | 3/2009 |
| WO | WO 2010/051349 A1 | 5/2010 |
| WO | WO 2011/070361 A1 | 6/2011 |
| WO | WO 2011/081628 A1 | 7/2011 |
| WO | WO 2012/084969 * | 6/2012 ............... A61K 9/70 |
| WO | WO 2012/084969 A1 | 6/2012 |

(56) References Cited

FOREIGN PATENT DOCUMENTS

| WO | WO 2012/089256 A1 | 7/2012 | |
| WO | WO 2012/097197 | * 7/2012 | ............... A61K 9/70 |
| WO | WO 2012/097197 A1 | 7/2012 | |
| WO | WO 2013/112806 A2 | 8/2013 | |
| WO | WO 2014/174564 A1 | 10/2014 | |
| WO | WO 2015/053878 A1 | 4/2015 | |
| WO | WO 2015/200472 A1 | 12/2015 | |
| WO | WO 2016/046675 A1 | 3/2016 | |
| WO | WO 2016/099198 A1 | 6/2016 | |
| WO | WO 2016/209982 A1 | 12/2016 | |
| WO | WO 2017/018321 A1 | 2/2017 | |
| WO | WO 2017/117554 A1 | 7/2017 | |
| WO | WO 2017/223402 A1 | 12/2017 | |
| WO | WO 2018/022814 A1 | 2/2018 | |
| WO | WO 2018/022815 A1 | 2/2018 | |
| WO | WO 2018/022816 A1 | 2/2018 | |
| WO | WO 2018/022817 A1 | 2/2018 | |
| WO | WO 2018/022818 A1 | 2/2018 | |

OTHER PUBLICATIONS

Chladek et al., "Steady-state bioequivalence studies of two memantine tablet and oral solution formulations in healthy volunteers", J. Appl. Biomed., vol. 6, pp. 39-45 (2008).

Choi et al., "Effect of fatty acids on the transdermal delivery of donepezil: in vitro and in vivo evaluation", Int. J. Pharm., vol. 422, No. 1-2, pp. 83-90 (2012).

Del Rio-Sancho, "Transdermal absorption of memantin—effect of chemical enhancers, iontophoresis, and role of enhancer lipophilicity", Eur J. Pharm. Biopharm., vol. 82, No. 1, pp. 164-170 (2012).

Fang et al., "Donepezil percutaneous absorption enhancer and back lining layer which includes polyethylene, polyester and ethylenevinyl acetate copolymer", Database WPI, AN 2013-G75464 (2013).

Forchetti, "Treating patients with moderate to severe Alzheimer's disease: implications of recent pharmacologic studies", Prim. Care Companion J. Clin. Psychiatry., vol. 7, No. 4, pp. 155-161 (2005).

Fornasari et al., "Synthesis and antioxidant properties of novel memantine derivatives", Cent. Nerv. Syst. Agents Med. Chem., vol. 17, No. 2, pp. 123-128 (2017).

International Search Report from International Application No. PCT/US2016/038792 dated Sep. 27, 2016.

International Search Report from International Patent Application No. PCT/US2017/038934 dated Oct. 10, 2017.

International Search Report from International Patent Application No. PCT/US2017/044047 dated Nov. 3, 2017.

International Search Report from International Patent Application No. PCT/US2017/044048 dated Nov. 3, 2017.

International Search Report from International Patent Application No. PCT/US2017/044049 dated Nov. 7, 2017.

International Search Report from International Patent Application No. PCT/US2017/044050 dated Nov. 6, 2017.

International Search Report from International Patent Application No. PCT/US2017/044051 dated Nov. 2, 2017.

International Search Report from International Patent Application No. PCT/US2018/043961, 6 pages, dated Nov. 23, 2018.

Kato, Patch used for treating Alzheimer-type dementia, comprises support portion, adhesive layer, donepezil and/or its hydrochloride, and additive chosen from isostearic acid, 2-cetyl ethylhexanoate, and hexadecyl isostearate, Database WPI, AN 2014-C88308 (2014).

Pastore et al., "Transdermal patches: history, development and pharmacology", Br. J. Pharmacol., vol. 172, No. 9, pp. 2179-2209 (2015).

Ravi and Gupta, "The treatment of alzheimers disease by using donopezil loaded transdermal patch", J. Chem. Pharm. Res., vol. 7, No. 3, pp. 806-813 (2015).

Schulz et al., "Therapeutic and toxic blood concentrations of nearly 1,000 drugs and other xenobiotics", Crit. Care, vol. 16, No. R136, 4 pgs. (2012).

Sozio et al., "Transdermal donepezil on the treatment of Alzheimer's disease", Neuropsychiatr. Dis. Treat, vol. 8, pp. 361-368 (2012).

Tiseo et al., "Pharmacokinetic and pharmacodynamic profile of donepezil HCl following evening administration", Br. J. Pharmacol., vol. 46, Suppl. 1, pp. 13-18 (1998).

Cabot Corporation, "Fumed Metal Oxides". 5 pages, Retreived from the internet on May 13, 2019 from http://www.cabotcorp.com/solutions/products-plus/fumed-metl-oxides (2019).

Del Rio-Sancho et al., "Transdermal therapeutic systems for memantine delivery. Comparison of passive and iontophoretic transport", Iot. J. Pharm., vol. 517, No. 1-2, pp. 104-111 (2017).

International Search Report from International Patent Application No. PCT/US2018/066848, 7 pages, dated Apr. 15, 2019.

Mittapelly et al., "In Depth Analysis of Pressure-Sensitive Adhesive Patch-Assisted Delivery of Memantine and Donepezil Using Physiologically Based Pharmacokinetic Modeling and in Vitro/in Vivo Correlations", Mol. Pharm., vol. 15, No. 7, pp. 2646-2655 (2018).

Shivalingam et al., "Formulation and evaluation of diclofenac potassium transdermal patches for enhanced therapeutic efficacy", Indian J. Res. Pharm. Biotechnol., pp. 1152-1157 (2014).

The Tamilnadu, "Formulation and evaluation of matrix type transdermal patched of benazepril hydrochloride", Dissertation submitted by R. Revathi, Reg. No. 26108606, to the Controller of Examination, Department of Pharmaceutics College of Pharmacy, Madurai Medical College, Madurai, 202 pages (2012).

Fong, "Pharmaceutical Application Guide and Exercises Analysis", Chinese Medical Science and Technology Press, pp. 460-462 (2011) *Chinese Language with English Translation*.

Jain et al., "High throuhput screening of transdermal penetration enhancers: Opportunities, methods, and applications", Percutaneous Penetration Enhancers, CRC Press, Chapter 22, pp. 319-333 (2005).

Lee and Lee, "pH-Controlled, Polymer-Mediated Assembly of Polymer Micelle Nanoparticles", Langmuir, vol. 23, pp. 488-495 (2007).

* cited by examiner

ADHESIVE MATRIX WITH HYDROPHILIC AND HYDROPHOBIC DOMAINS AND A THERAPEUTIC AGENT

CROSS-REFERENCE TO RELATED APPLICATIONS

This application is a U.S. National Phase Application under 35 U.S.C. § 371 of International Application No. PCT/US2017/038934, with an International Filing Date of Jun. 23, 2017, which claims priority to U.S. Provisional Application No. 62/353,891, filed Jun. 23, 2016, each of which is hereby incorporated by reference in its entirety.

TECHNICAL FIELD

The subject matter described herein relates to transdermal administration of drugs for both local and systemic delivery, and formulations for use in such methods.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

The skin is the largest organ of the human body. It is easily accessible, has an excellent blood supply, and presents an ideal location to administer therapeutic agents. However, the primary function of the skin is to act as a permoselective barrier, inhibiting the penetration of molecules and unwanted compounds into the body, thereby making drug delivery via the skin difficult. Strategies designed to overcome the barrier properties of the skin include the use of chemical penetration enhancers, supersaturation, and altering the integrity of the skin, for example by electrophoresis or iontophoresis. Chemical penetration enhancers work by increasing the solubility of a drug in the skin, enhancing partitioning and hence permeation. Supersaturation of a therapeutic agent in a transdermal system increases the thermodynamic activity of the agent to thereby enhance permeation rate. When a drug is saturated in a vehicle, the thermodynamic activity is equal to one (i.e., unity). Since drug thermodynamic activity is proportional to drug permeation rate, increasing the thermodynamic activity should increase permeation rate. However, supersaturated formulations are physically unstable and, over time, the drug in a supersaturated solution will precipitate, and this loss of drug from solution will eventually result in a return to a more stable saturated state. Accordingly, to date, this approach has found limited applicability in practice.

BRIEF SUMMARY

The following aspects and embodiments thereof described and illustrated below are meant to be exemplary and illustrative, not limiting in scope.

In one aspect, an adhesive matrix comprised of a hydrophilic domain and a hydrophobic domain, and a therapeutically active agent contained therein in a supersaturated condition, is provided. The hydrophilic domain is comprised of a polyvinylpyrrolidone-vinyl acetate copolymer and the hydrophobic domain comprises one or both of a polyisobutylene and an acrylic acid/vinyl acetate copolymer. The active agent is characterized by (a) a melting point of less than about 250° C. or (b) a solubility in water of less than about 500 mg/L or (c) an oil/water partition coefficient of between about 2.1 and about 5. The hydrophilic domain and the hydrophobic domain are co-soluble in a solvent system and the proportion of the hydrophilic domain and hydrophobic domain is selected to optimize, or maximize, solubility of active agent in the matrix. In one embodiment, the matrix comprises an amount of active agent greater than the amount of active agent soluble in either domain alone. In another embodiment, the matrix comprises an amount of active agent greater than the amount of active agent soluble in the hydrophobic domain alone. In another embodiment, the matrix comprises an amount of active agent greater than the amount of active agent soluble in the hydrophilic domain alone.

In one embodiment, the hydrophobic domain comprises a combination of polyisobutylene and polybutene. In another embodiment, the hydrophobic domain comprises an acrylic acid/vinyl acetate copolymer.

In another embodiment, the adhesive matrix comprises between about 10-25 wt % hydrophilic domain. In still another embodiment, the adhesive matrix comprises between about 35-80 wt % hydrophobic domain.

In still another embodiment, the adhesive matrix comprises about 15-25 wt % active agent, about 50-60 wt % acrylate adhesive, about 7-15 wt % polyisobutylene and polybutene mixture, and about 10-20 wt % polyvinylpyrrolidone-vinyl acetate copolymer.

In yet another embodiment, the active agent is selected from the group of drugs consisting of donepezil, ropinrole, lidocaine, and oxybutynin.

In another aspect, a device for transdermal administration of an active agent is provided, where the device comprises an adhesive matrix layer as described herein.

In still another aspect, a formulation for preparation of an adhesive matrix is provided. The formulation, in one embodiment, comprises between about 10-25 wt % polyvinylpyrrolidone-vinyl acetate copolymer and between about 40-64 wt % of an acrylate adhesive, and about 5-50 wt % of an active agent in a solvent system. The solvent system, in one embodiment, comprises an organic solvent in which the polyvinylpyrrolidone-vinyl acetate copolymer is soluble and in which a polyvinylpyrrolidone homopolymer is insoluble.

In one embodiment, the formulation additionally comprises about 35-75 wt % of polyisobutylene and polybutene. In this embodiment, the solvent system comprises a solvent in which the polyisobutylene and polybutene and the polyvinylpyrrolidone-vinyl acetate copolymer are soluble.

In another aspect, a method for the manufacture of an adhesive matrix is provided. In one embodiment, the method comprises solubilizing a polyvinylpyrrolidone-vinyl acetate copolymer in a first solvent; solubilizing polyisobutylene and polybutene in a second solvent; mixing the two to form a homogeneous solution; adding to the homogeneous solution an acrylate adhesive solubilized in a third solvent to form an adhesive solution; adding to the adhesive solution an active agent; and forming an adhesive matrix from the adhesive solution with active agent.

In another embodiment, the method comprises solubilizing a polyvinylpyrrolidone-vinyl acetate copolymer in a first solvent; solubilizing an acrylate adhesive in a second solvent; mixing the two to form an adhesive solution; adding to the adhesive solution an active agent; and forming an adhesive matrix from the adhesive solution with active agent.

In one embodiment, the acrylate adhesive is not a methacrylate copolymer.

In another embodiment, the polyvinylpyrrolidone-vinyl acetate copolymer is a copolymer of n-vinyl-2-pyrrolidone and a vinyl acetate that is not ethylhexyl acrylate. That is, the acrylate is not 2-ethylhexyl acrylate-vinyl pyrrolidone copolymer.

In one embodiment, the polyvinylpyrrolidone-vinyl acetate copolymer is a linear random copolymer of n-vinyl-2-pyrrolidone and vinyl acetate. In one embodiment, the copolymer is a 60:40 copolymer of n-vinyl-2-pyrrolidone and vinyl acetate. In still another embodiment, the acrylate adhesive is an acrylic acid/vinyl acetate copolymer, excluding methacrylic acid/vinyl acetate copolymers.

In yet another embodiment, the acrylic acid/vinyl acetate copolymer is one without a cross-linker agent and has a viscosity between about 2000-8000 mPa-s when measured at 25° C.

In one embodiment, the first solvent is one in which polyvinylpyrrolidone homopolymer is insoluble. For example, and in one embodiment, the first solvent comprises toluene. In another embodiment, the first solvent comprises a mixture of toluene and iso-propyl alcohol. In one embodiment, the mixture comprises 9 parts toluene and 1 part iso-propyl alcohol, w/w. In another embodiment, the mixture comprises 9 parts toluene and 1 part iso-propyl alcohol, v/v.

In another embodiment, the second solvent is the same as the first solvent. In still another embodiment, the first solvent is a mixture comprising toluene and the second solvent is toluene.

In one embodiment, the solvent for the acrylate adhesive, sometimes referred to as a second solvent or as a third solvent, is ethyl acetate.

In one embodiment, forming an adhesive matrix comprises applying the adhesive solution with the active agent onto a substrate and drying at a temperature of between 50-100° C.

In another embodiment, the adhesive matrix comprises 15-25 wt % active agent, 50-60 wt % acrylate adhesive, 7-15 wt % polyisobutylene and polybutene mixture and 10-20 wt % polyvinylpyrrolidone-vinyl acetate copolymer.

The matrix, formulation and method can comprise as an active agent a drug selected from the group consisting of donepezil, ropinrole, lidocaine, and oxybutynin.

In addition to the exemplary aspects and embodiments described above, further aspects and embodiments will become apparent by reference to the examples and by study of the following descriptions.

Additional embodiments of the present methods and compositions, and the like, will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples.

DETAILED DESCRIPTION

I. Definitions

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

II. Adhesive Formulation and Adhesive Matrix

The adhesive matrix described herein is comprised of a hydrophilic domain and a hydrophobic domain, and a therapeutically active agent contained in the matrix in a supersaturated, stable, condition. The hydrophilic domain and the hydrophobic domain are co-soluble in a solvent system, to provide a homogeneous blend in which the active agent is solubilized. The proportion of the hydrophilic domain and hydrophobic domain is selected to optimize, or maximize, solubility of active agent in the matrix. For example, and in one embodiment, the matrix comprises an amount of active agent greater than the amount of active agent soluble in the hydrophobic domain alone or, in another embodiment, the hydrophilic domain alone, or, in yet another embodiment, in both domains alone. In one embodiment, the amount of active agent in the matrix is about the saturation concentration of the active agent in the hydrophobic domain alone or, in another embodiment, the hydrophilic domain alone, or, in yet another embodiment, in both domains alone.

The hydrophilic domain is comprised of a polyvinylpyrrolidone-vinyl acetate copolymer and the hydrophobic domain comprises one or both of a polyisobutylene and an acrylic acid/vinyl acetate copolymer.

Polyvinylpyrrolidone-vinyl acetate copolymers are linear, random copolymers produced by the free-radical polymerization of the monomers N-vinyl-2-pyrrolidone (NVP) and vinyl acetate (VA). The amount of each monomer can be varied to product copolymers with ratios varying from 70/30 to 30/70 vinyl acetate to vinylpyrrolidone. In one embodiment, the copolymer comprises 30% vinylpyrrolidone; in another embodiment, the copolymer comprises 50% vinylpyrrolidone content; in another embodiment, the copolymer comprises 60% vinylpyrrolidone content; and in another embodiment, the copolymer comprises 70% vinylpyrrolidone content. In one embodiment, the polyvinylpyrrolidone-vinyl acetate copolymer results from polymerization of an n-vinyl-2-pyrrolidone monomer and a vinyl acetate monomer that is not ethylhexyl acrylate.

The molecular weight of polyvinylpyrrolidone-vinyl acetate copolymers may vary, and copolymers in a range of molecular weights are commercially available. In one embodiment, a polyvinylpyrrolidone-vinyl acetate copolymer with a molecular weight (weight average) is between 40,000-60,000 Daltons, and in another embodiment, is between about 25,000-200,000 Daltons.

In the working examples set forth hereinbelow, a polyvinylpyrrolidone-vinyl acetate copolymer comprised of 60% vinylpyrrolidone content and a weight average molecular weight of 47,000 Daltons was used.

The hydrophobic domain in the adhesive matrix comprises one or both of a polyisobutylene and an acrylic acid/vinyl acetate copolymer. In another embodiment, the hydrophobic domain in the adhesive matrix comprises an acrylic acid/vinyl acetate copolymer, and optionally, a polyisobutylene.

In one embodiment, a polyisobutylene is a blend or a mixture of a high molecular weight polyisobutylene and a medium molecular weight polyisobutylene. The term, "high molecular weight polyisobutylene" refers to a polyisobutylene having an average molecular weight in the range of about 450,000 to about 2,100,000 Daltons. and preferably from about 500,000 to about 1,500.000 Daltons. The term. "medium molecular weight polyisobutylene" refers to a polyisobutylene having an average molecular weight in the range of about 10,000 to about 450,000 Daltons. and preferably from about 25,000 to about 100,000 Daltons.

In the working examples set forth hereinbelow, a high molecular weight polyisobutylene of 1,000,000 Daltons and a medium molecular weight polyisobutylene of about 50,000 Daltons were blended in a ratio of 1:5. Stated alternatively, on a 100 weight basis, the matrix comprised a ratio of high molecular weight polyisobutylene to medium molecular weight polyisobutylene of 17:83. In other embodiments, the adhesive matrix contains a high molecular weight polyisobutylene to medium molecular weight polyisobutylene ratio of between about 5-40:95-60, or between about 10-25:90-75 or between about 10-20:90-80.

In another embodiment, the polyisobutylene (also referred to as a polyisobutylenen blend) in the hydrophobic domain further comprises a polybutene. Polybutene is a viscous, non-drying, liquid polymer, prepared by the copolymerization of 1- and 2-butene with a small quantity of isobutylene. The polybutene in one embodiment has a molecular weight of between about 750-6000 Daltons, preferably between about 900-4000 Daltons, and preferably between about 900-3000 Daltons. In the working examples below, some embodiments of the hydrophobic domain comprised a polybutene of 2500 Dalton molecular weight, present in the polyisobutylene blend at 40 weight percent. More generally, the polybutene is present in the polyisobutylene blend of the hydrophobic domain in an amount between 20-50 weight percent, or between 25-45 weight percent.

The hydrophobic domain of the adhesive matrix comprises an acrylic polymer pressure sensitive adhesive. An acrylic polymer pressure sensitive adhesive intends a polyacrylate adhesive that is a polymer or a copolymer of a monomer or monomers selected from acrylic acid esters and methacrylic acid esters. Other monomers, such as acrylic acid and vinyl acetate, may be present. In one embodiment, the acrylate adhesive is not a methacrylate copolymer; that is, the polyacrylate adhesive excludes a methacrylic acid monomeric unit. Preferably the acrylic polymer pressure sensitive adhesive has pendent carboxyl (—COOH) or hydroxyl (—OH) functional groups attached to the polymer chain.

In one embodiment, the acrylic acid/vinyl acetate copolymer is one without a cross-linker agent. The exclusion of cross-linker agents containing metals, particularly transition metal cross-linking agents, which act as catalysts of several chemical reactions, such as esterification, transesterification, oxidation and addition, avoids the possibility of chemical interaction with the active agent in the matrix and a possible loss of potency, impurity formation and stability problems. Preferably the adhesive matrix layer contains no component acting as a cross-linking agent for the acrylic polymer.

In one embodiment, the acrylic acid/vinyl acetate copolymer has a viscosity between about 2000-8000 mPa-s when measured at 25° C.

The adhesive matrix can include additives and excipients as is common in the art. By way of example, the matrix can include penetration enhancers such as fatty acids having a carbon number of 6-20, aliphatic alcohols, fatty acid esters or ethers or amides, aromatic organic acids, aromatic alcohols, aromatic organic acid esters or ethers (saturated or unsaturated, and either cyclic, straight chain or branched), furthermore, lactic acid esters, acetic acid esters, monoterpene compounds, sesquiterpene compounds, Azone, Azone derivatives, glycerin fatty acid esters, sorbitan fatty acid esters, polyethylene glycol fatty acid esters, polyoxyethylene alkyl ethers, polyoxyethylene hardened castor oil (HCO), sucrose fatty acid esters and the like. Fatty acids having a carbon number of 8 or more (such as caprylic acid, capric acid, myristic acid, palmitic acid, oleic acid, stearic acid, etc.), and aliphatic alcohols (such as oleyl alcohol, isostearyl alcohol, lauryl alcohol, octyl alcohol, decyl alcohol, myristyl alcohol, cetyl alcohol, stearyl alcohol, etc.) are contemplated. The amount of enhancer is, taking into consideration the sufficient permeability of active components into the skin and skin irritation as adhesive patches, between about 1-10 wt %, or about 2-8 wt %, and or about 3-6 wt % relative to the weight of the adhesive matrix.

Additives such as antioxidants, fillers, preservatives and ultraviolet absorbers may be blended in the adhesive matrix. As antioxidants, tocopherol and its ester derivatives, ascorbic acid, ascorbic acid-stearic acid ester, nordihydroguaretic acid, dibutyl hydroxy toluene (BHT), butyl hydroxy anisole and the like are preferred. As fillers, calcium carbonate, magnesium carbonate, silicates (such as aluminum silicate, magnesium silicate, etc.), silicic acid, barium sulfate, calcium sulfate, calcium zincate, zinc oxide, titanium oxide and the like are preferred. As preservatives, ethyl p-hydroxybenzoate, propyl p-hydroxybenzoate, butyl p-hydroxybenzoate and the like are preferred. As ultraviolet absorbers, p-aminobenzoic acid derivatives, anthranilic acid derivatives, salicylic acid derivatives, coumarin derivatives, amino-acid compounds, imidazoline derivatives, pyrimidine derivatives, dioxane derivatives and the like are preferred. These additives may be present in the adhesive matrix at an amount of preferably 10 wt % or less, more preferably 5 wt % or less, and especially preferably 2 wt % or less.

The adhesive matrix also comprises a therapeutically active agent. The active agent is characterized by (a) a melting point of less than about 250° C. or (b) a solubility in water of less than about 500 mg/L or (c) an oil/water partition coefficient of between about 2.1 and about 5. Examples of active agents are set forth in the table below, and include donepezil, ropinrole, lidocaine, and oxybutynin.

| Active Agent (base) | Water solubility | Melting Point (° C.) | LogP |
|---|---|---|---|
| donepezil | 2.931 mg/L (pubchem.ncbi.nlm.nih.gov) | 206.7 | 4.86 |
| ropinole | 133 mg/mL | 243-250 | 2.7 |
| lidocaine | 410 mg/L at 30 C. | 68 | 2.26 |
| oxybutynin | 10 mg/L (drugbank.ca) | 129-130 | 4.3 |

Adhesive formulations and matrices were prepared to illustrate the concepts described above. Examples 1-10 set forth exemplary formulations and resulting adhesive matrices using the active agent donezepil, in its base form, as a model drug.

In Example 1, an adhesive matrix comprising 66 wt % of a hydrophobic domain and 14% of a hydrophilic domain was prepared, with the active agent present at 20 wt % in the matrix. The active agent was present at a concentration above its saturation concentration in the hydrophobic domain alone, due to the presence of the hydrophilic domain, which lowered the solubility of the hydrophobic domain for the active agent. Accordingly, the active agent was present in the adhesive matrix at a supersaturated concentration, to thereby provide a thermodynamic activity greater than unity to provide a maximum driving force for permeation of the agent across the skin. The hydrophobic domain in the exemplary adhesive matrix of Example 1 was comprised of a homogeneous blend of an acrylic acid/vinyl acetate copolymer and a polyisobutylene mixture of a high molecular weight polyisobutylene, a medium molecular weight polyisobutylene, and a polybutene. The blend had 86 parts of the acrylic acid/vinyl acetate copolymer and 14 parts of polyisobutylene mixture.

In Example 2, an adhesive matrix comprising 62 wt % of a hydrophobic domain and 13% of a hydrophilic domain was prepared, with the active agent present at 20 wt % in the matrix. The active agent was present at a concentration above its saturation concentration in the hydrophobic domain alone, due to the presence of the hydrophilic domain, which lowered the solubility of the hydrophobic domain for the active agent. Accordingly, the active agent was present in the adhesive matrix at a supersaturated concentration, to thereby provide a thermodynamic activity greater than unity to provide a maximum driving force for permeation of the agent across the skin. The hydrophobic domain in the exemplary adhesive matrix of Example 2 was comprised of a homogeneous blend of an acrylic acid/vinyl acetate copolymer and a polyisobutylene mixture of a high molecular weight polyisobutylene, a medium molecular weight polyisobutylene, and a polybutene. The blend had 93 parts of the acrylic acid/vinyl acetate copolymer and 7 parts of polyisobutylene mixture. The adhesive matrix additionally included a penetration enhancer.

In Example 3, an adhesive matrix comprising 62 wt % of a hydrophobic domain and 13% of a hydrophilic domain was prepared, with the active agent present at 20 wt % in the matrix. The hydrophobic domain in the exemplary adhesive matrix of Example 3 was comprised of a homogeneous blend of an acrylic acid/vinyl acetate copolymer and a polyisobutylene mixture of a high molecular weight polyisobutylene, a medium molecular weight polyisobutylene, and a polybutene. The blend had 85 parts of the acrylic acid/vinyl acetate copolymer and 15 parts of polyisobutylene mixture. The adhesive matrix additionally included a penetration enhancer.

In Example 4, an adhesive matrix comprising 62 wt % of a hydrophobic domain and 5 wt % of a hydrophilic domain was prepared, with the active agent present at 20 wt % in the matrix. The hydrophobic domain in the exemplary adhesive matrix of Example 4 was comprised of a homogeneous blend of an acrylic acid/vinyl acetate copolymer and a polyisobutylene mixture of a high molecular weight polyisobutylene, a medium molecular weight polyisobutylene, and a polybutene. The blend had 79 parts of the acrylic acid/vinyl acetate copolymer and 21 parts of polyisobutylene mixture. The adhesive matrix additionally included a penetration enhancer.

In Example 5, an adhesive matrix comprising 57 wt % of a hydrophobic domain and 13 wt % of a hydrophilic domain was prepared, with the active agent present at 20 wt % in the matrix. The hydrophobic domain in the exemplary adhesive matrix of Example 5 was comprised of a homogeneous blend of an acrylic acid/vinyl acetate copolymer and a polyisobutylene mixture of a high molecular weight polyisobutylene, a medium molecular weight polyisobutylene, and a polybutene. The blend had 77 parts of the acrylic acid/vinyl acetate copolymer (44/57) and 22 parts (13/57) of polyisobutylene mixture. The adhesive matrix additionally included a penetration enhancer.

In Example 6, an adhesive matrix comprising 45 wt % of a hydrophobic domain and 15 wt % of a hydrophilic domain was prepared, with the active agent present at 40 wt % in the matrix. The hydrophobic domain in the exemplary adhesive matrix of Example 6 was comprised of an acrylic acid/vinyl acetate copolymer.

In Example 7, an adhesive matrix comprising 42 wt % of a hydrophobic domain and 14 wt % of a hydrophilic domain was prepared, with the active agent present at 40 wt % in the matrix. The hydrophobic domain in the exemplary adhesive matrix of Example 7 was comprised of an acrylic acid/vinyl acetate copolymer. The adhesive matrix additionally included a penetration enhancer.

In Examples 8-10, adhesive matrices comprised of a hydrophobic domain and a hydrophilic domain of a polyvinylpyrrolidone homopolymer are set forth.

The table below summarizes the weight ratios of the hydrophobic domain to hydrophilic domain in the exemplary adhesive matrices of Examples 1-10, and also shows the ratio of drug to hydrophobic domain.

| Example No. | Ratio Hydrophobic Domain/Hydrophilic Domain | Ratio Drug/ Hydrophobic Domain |
|---|---|---|
| 1 | 4.67 | 3.29 |
| 2 | 4.68 | 3.09 |
| 3 | 4.77 | 3.1 |
| 4 | 12.4 | 3.1 |
| 5 | 4.38 | 2.85 |
| 6 | 3.0 | 1.12 |
| 7 | 3.0 | 1.05 |
| 8 | 6.37 | 1.28 |
| 9 | 6.4 | 2.59 |
| 10 | 6.39 | 4.90 |

Preparation of Adhesive Matrix and Transdermal Device

In another aspect, a formulation for preparation of an adhesive matrix is provided. The formulation comprises, in one embodiment, between about 10-25 wt % polyvinylpyrrolidone-vinyl acetate copolymer and about 40-64 wt % of an acrylate adhesive and about 5-50 wt % of an active agent in a solvent system. In one embodiment, the solvent system is comprised of an organic solvent in which the polyvinylpyrrolidone-vinyl acetate copolymer is soluble and a polyvinylpyrrolidone homopolymer is insoluble. In one embodiment, the solvent system is a binary mixture of organic solvents, and in another embodiment, is a ternary mixture.

A method for the manufacture of an adhesive matrix is also provided. With reference to Example 1, the method comprises (i) solubilizing a polyvinylpyrrolidone-vinyl acetate copolymer in a first solvent; (ii) solubilizing polyisobutylene and polybutene (when present in the formulation) in a second solvent; (iii) mixing (i) and (ii) to form a homogeneous solution; (iv) adding to the homogeneous solution an acrylate adhesive solubilized in a third solvent to form an adhesive solution; (v) adding to the adhesive solution an active agent as described herein, and (v) forming an adhesive matrix from the adhesive solution with the active agent that comprises between about 35-80 wt % acrylate, between about 0.01-30 wt % polyisobutylene and polybutene mixture, between about 10-25 wt % polyvinylpyrrolidone-vinyl acetate copolymer, and between about 5-50 wt % active agent.

In another embodiment, the method comprises (i) solubilizing a polyvinylpyrrolidone-vinyl acetate copolymer in a first solvent; (ii) solubilizing an acrylate adhesive in a second solvent; (iii) mixing (i) and (ii) to form a homogeneous solution; (iv) adding to the homogeneous solution an active agent as described herein, and (v) forming an adhesive matrix from the solution of (iv). In one embodiment, the adhesive matrix formed from the solution comprises between about 35-80 wt % acrylate, between about 10-25 wt % polyvinylpyrrolidone-vinyl acetate copolymer, and between about 5-50 wt % active agent.

In forming the adhesive matrix, the formulation is cast onto a suitable film, such as a release liner film, dried to eliminate all volatile compounds at temperature or temperatures in the range between 50° C. and 100° C.

To form a transdermal device, the adhesive matrix is then laminated to a suitable film, generally to a backing film. Backing films are known in the industry and any that provide support for the adhesive layer and are impermeable or substantially impermeable to the active agent can be used. It can be flexible or nonflexible. Suitable materials are well known to the art and include, without limitation, polyethylene terephthalate, various nylons, polypropylene, metalized polyester films, polyvinylidene chloride, and aluminum foil. In other embodiments, the transdermal device may comprise a fabric or tie layer in the adhesive matrix, and any stretch or nonstretch material may be used. For example, fabric and non-woven fabric material including polyesters such as polyethylene terephthalate, polyurethane, polyvinyl acetate, polyvinylidene chloride and polyethylene, may be used.

III. Examples

The following examples are illustrative in nature and are in no way intended to be limiting.

Example 1

Adhesive Formulation, Adhesive Matrix and Transdermal Devices Comprising Donepezil A formulation for a hydrophilic domain was prepared by dissolving a polyvinylpyrrolidone vinyl acetate copolymer (Plasdone S-630) in a 9:1 mixture of toluene and isopropyl alcohol to yield a solution with 35 wt % polyvinylpyrrolidone vinyl acetate copolymer. A formulation for a hydrophobic domain was prepared by dissolving a blend of a high molecular weight polyisobutylene homopolymer (Oppanol B-100; 1,000,000 Dalton molecular weight) and a medium moleculear weight polyisobutylene homopolymer (Oppanol B-12; 50,000 Dalton molecular weight) with polybutene (Indopol H-1900) in a ratio of 1:5:4 in toluene, where the polyisobutylene blend was at a concentration of 60 wt %.

An acrylate adhesive solution was prepared by dissolving an acrylic acid/vinyl acetate copolymer (DuroTak 87-2015) in ethyl acetate at a concentration of 51.5 wt %.

An adhesive formulation was prepared as follows. 2.017 g of the hydrophilic domain formulation was mixed with 0.784 g of the hydrophobic domain formulation until a homogeneous solution was formed. An additional 2.49 g of toluene and 0.72 g of isopropyl alcohol were added and the solution was well mixed. Next, 5.483 g of the acrylate adhesive solution was added, mixing until homogeneous. Then, 1.00 g of donepezil base was added and dissolved with vortexing.

An adhesive matrix was prepared by coating the adhesive formulation onto a silicon-coated release liner at a wet thickness of 20 mils and then drying at 70° C. for 20 minutes. The adhesive matrix had a final composition as follows:

| Adhesive Matrix No. 1 | | |
|---|---|---|
| Hydrophobic Domain - 65.8 wt % | acrylic acid/vinyl acetate copolymer | 56.47 wt % |
| | polyisobutylene homopolymer blend/polybutene | 9.41 wt % |
| Hydrophilic Domain - 14.1 wt % | polyvinylpyrrolidone vinyl acetate copolymer | 14.12 wt % |
| Active Agent - 20 wt % | donepezil base | 20 wt % |

A backing layer (Scotchpak 9732) was then laminated onto the matrix and transdermal devices of 10 cm2 were die cut from the laminate.

Example 2

Adhesive Formulation, Adhesive Matrix and Transdermal Devices Comprising Donepezil An adhesive formulation was prepared as described in Example 1 to yield an adhesive matrix with the following composition:

| Adhesive Matrix No. 2 | | |
|---|---|---|
| Hydrophobic Domain - 61.8 wt % | acrylic acid/vinyl acetate copolymer | 57.4 wt % |
| | polyisobutylene homopolymer blend/polybutene | 4.40 wt % |
| Hydrophilic Domain - 13.2 wt % | polyvinylpyrrolidone vinyl acetate copolymer | 13.2 wt % |
| Active Agent - 20 wt % | donepezil base | 20.0 wt % |
| Penetration Enhancer | Lauryl lactate | 5.0 wt % |

Example 3

Adhesive Formulation, Adhesive Matrix and Transdermal Devices Comprising Donepezil An adhesive formulation was prepared as described in Example 1 to yield an adhesive matrix with the following composition:

| Adhesive Matrix No. 3 | | |
|---|---|---|
| Hydrophobic Domain - 62.0 wt % | acrylic acid/vinyl acetate copolymer | 53.0 wt % |
| | polyisobutylene homopolymer blend/polybutene | 9.0 wt % |
| Hydrophilic Domain - 13.0 wt % | polyvinylpyrrolidone vinyl acetate copolymer | 13.0 wt % |
| Active Agent - 20.0 wt % | donepezil base | 20.0 wt % |
| Penetration Enhancer | Lauryl lactate | 5.0 wt % |

Example 4

Adhesive Formulation, Adhesive Matrix and Transdermal Devices Comprising Donepezil An adhesive formulation was prepared as described in Example 1 to yield an adhesive matrix with the following composition:

| Adhesive Matrix No. 4 | | |
|---|---|---|
| Hydrophobic Domain - 62.0 wt % | acrylic acid/vinyl acetate copolymer | 49.0 wt % |
| | polyisobutylene homopolymer blend/polybutene | 13.0 wt % |
| Hydrophilic Domain - 5.0 wt % | polyvinylpyrrolidone vinyl acetate copolymer | 5.0 wt % |
| Active Agent - 20 wt % | donepezil base | 20.0 wt % |
| Penetration Enhancer | Lauryl lactate | 5.0 wt % |

Example 5

Adhesive Formulation, Adhesive Matrix and Transdermal Devices Comprising Donepezil An adhesive formulation was prepared as described in Example 1 to yield an adhesive matrix with the following composition:

| Adhesive Matrix No. 5 | | |
|---|---|---|
| Hydrophobic Domain - 57.0 wt % | acrylic acid/vinyl acetate copolymer | 44.0 wt % |
| | polyisobutylene homopolymer blend/polybutene | 13.0 wt % |
| Hydrophilic Domain - 13.0 wt % | polyvinylpyrrolidone vinyl acetate copolymer | 13.0 wt % |
| Active Agent - wt % | donepezil base | 20.0 wt % |
| Penetration Enhancer | Lauryl lactate | 5.0 wt % |

Example 6

Adhesive Formulation, Adhesive Matrix and Transdermal Devices Comprising Donepezil An adhesive formulation was prepared as described in Example 1 to yield an adhesive matrix with the following composition:

| Adhesive Matrix No. 6 | | |
|---|---|---|
| Hydrophobic Domain - 45.0 wt % | acrylic acid/vinyl acetate copolymer | 45.0 wt % |
| | polyisobutylene homopolymer blend/polybutene | 0.0 wt % |
| Hydrophilic Domain - 15.0 wt % | polyvinylpyrrolidone vinyl acetate copolymer | 15.0 wt % |
| Active Agent - 40.0 wt % | donepezil base | 40.0 wt % |

Example 7

Adhesive Formulation, Adhesive Matrix and Transdermal Devices Comprising Donepezil An adhesive formulation was prepared as described in Example 1 to yield an adhesive matrix with the following composition:

| Adhesive Matrix No. 7 | | |
|---|---|---|
| Hydrophobic Domain - 42.0 wt % | acrylic acid/vinyl acetate copolymer | 42.0 wt % |
| | polyisobutylene homopolymer blend/polybutene | 0.0 wt % |
| Hydrophilic Domain - 14.0 wt % | polyvinylpyrrolidone vinyl acetate copolymer | 14.0 wt % |
| Active Agent - 40.0 wt % | donepezil base | 40.0 wt % |
| Penetration Enhancer | lauryl lactate | 4.0 wt % |

Example 8

Adhesive Formulation, Adhesive Matrix and Transdermal Devices Comprising Donepezil An adhesive formulation was prepared as described in Example 1 to yield an adhesive matrix with the following composition:

| Adhesive Matrix No. 8 | | |
|---|---|---|
| Hydrophobic Domain - 51.6 wt % | acrylic acid/vinyl acetate copolymer | 51.61 wt % |
| | polyisobutylene homopolymer blend/polybutene | 0.0 wt % |
| Hydrophilic Domain - 8.1 wt % | polyvinylpyrrolidone (Kollidone 90K) | 8.06 wt % |
| Active Agent - 40.32 wt % | donepezil base | 40.32 wt % |

Example 9

Adhesive Formulation, Adhesive Matrix and Transdermal Devices Comprising Donepezil An adhesive formulation was prepared as described in Example 1 to yield an adhesive matrix with the following composition:

| Adhesive Matrix No. 9 | | |
|---|---|---|
| Hydrophobic Domain - 64.8 wt % | acrylic acid/vinyl acetate copolymer | 64.8 wt % |
| | polyisobutylene homopolymer blend/polybutene | 0.0 wt % |
| Hydrophilic Domain - 10.1 wt % | polyvinylpyrrolidone (Kollidone 90K) | 10.14 wt % |
| Active Agent - 25 wt % | donepezil base | 25.0 wt % |

Example 10

Adhesive Formulation, Adhesive Matrix and Transdermal Devices Comprising Donepezil An adhesive formulation was prepared as described in Example 1 to yield an adhesive matrix with the following composition:

| Adhesive Matrix No. 10 | | |
|---|---|---|
| Hydrophobic Domain - 73.5 wt % | acrylic acid/vinyl acetate copolymer | 73.51 wt % |
| | polyisobutylene homopolymer blend/polybutene | 0.0 wt % |
| Hydrophilic Domain - 11.5 wt % | polyvinylpyrrolidone (Kollidone 90K) | 11.49 wt % |
| Active Agent - 15 wt % | donepezil base | 15.0 wt % |

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. An adhesive matrix, comprising:
a hydrophilic domain consisting of a polyvinylpyrrolidone-vinyl acetate copolymer;
a hydrophobic domain consisting of a polyisobutylene and polybutene mixture and an acrylic acid/vinyl acetate copolymer, wherein the polyisobutylene and polybutene mixture is present in an amount of about 7-15 wt % based on the total weight of the adhesive matrix, and the acrylic acid/vinyl acetate copolymer is present in an amount of about 50-60 wt %, based on the total weight of the adhesive matrix; and
an active agent selected from the group consisting of donepezil, ropinrole, lidocaine, and oxybutynin;
wherein the active agent is present in an amount of about 15-25 wt % based on the total weight of the adhesive matrix, and wherein the active agent is present at a concentration above its saturation concentration in the hydrophobic domain;
wherein the hydrophilic domain and the hydrophobic domain are co-soluble in a solvent system and present in the adhesive matrix in a proportion to one another to solubilize an amount of the active agent greater than the amount of the active agent soluble in either domain alone, and
wherein the adhesive matrix does not contain any component acting as a cross-linking agent for the acrylic polymer.

2. The adhesive matrix of claim 1, wherein the polyisobutylene and polybutene mixture comprises a high molecular weight polyisobutylene having an average molecular weight ranging from about 500,000 to about 1,500.000 Daltons and a medium molecular weight polyisobutylene having an average molecular weight ranging from about 25,000 to about 100,000 Daltons.

3. The adhesive matrix of claim 1, comprising between 10-25 wt % hydrophilic domain.

4. The adhesive matrix of claim 1, comprising between about 35-80 wt % hydrophobic domain.

5. The adhesive matrix of claim 1, wherein the polyvinylpyrrolidone-vinyl acetate copolymer is about 10-20 wt %.

6. A device for transdermal administration of an active agent, the device comprising an adhesive matrix layer according to claim 1.

7. The adhesive matrix of claim 1, wherein the acrylic acid/vinyl acetate copolymer is not a methacrylate copolymer.

* * * * *